United States Patent [19]

Cordier et al.

[11] Patent Number: 5,554,573
[45] Date of Patent: Sep. 10, 1996

[54] RANEY-TYPE CATALYSTS FOR THE HYDROGENATION OF HALONITROAROMATIC COMPOUNDS

[75] Inventors: Georges Cordier, Francheville; Jean-Pierre Damon, Le Touvet; Pierre Fouilloux, Caluire et Cuire; Philippe Marion, Villeurbanne, all of France

[73] Assignee: Rhone-Poulenc Chimie, Courbevoie Cedex, France

[21] Appl. No.: 319,643

[22] Filed: Oct. 7, 1994

[30] Foreign Application Priority Data

Oct. 7, 1993 [FR] France .................................. 93 12149

[51] Int. Cl.⁶ ....................................................... B01J 25/02
[52] U.S. Cl. ........................................... 502/301; 502/314
[58] Field of Search ..................................... 502/301, 314

[56] References Cited

U.S. PATENT DOCUMENTS

| 4,089,812 | 5/1978 | O'Hare et al. | 252/466 J |
| 4,297,509 | 10/1981 | Chiasson | 562/456 |
| 4,503,251 | 5/1985 | Gray et al. | 564/450 |
| 4,904,774 | 2/1990 | McDaniel, Jr. et al. | 536/127 |

FOREIGN PATENT DOCUMENTS

| 0325892 | 8/1989 | European Pat. Off. . |
| 0409709 | 1/1991 | European Pat. Off. . |
| 2057821 | 5/1971 | France . |
| 2175910 | 12/1986 | United Kingdom . |

*Primary Examiner*—Shrive Beck
*Assistant Examiner*—Timothy H. Meeks
*Attorney, Agent, or Firm*—Burns, Doane, Swecker & Mathis, L.L.P.

[57] ABSTRACT

Halonitroaromatic compounds, e.g., 3-chloro-4-fluoronitrobenzene, are selectively hydrogenated into the corresponding haloaromatic amines, in the essential absence of hydrodehalogenation, by reacting same with hydrogen in the presence of a catalytically effective amount of a novel Raney-type catalyst composition consisting essentially of an alloy of nickel, aluminum and molybdenum, Ni/Al/Mo, the Al/Mo ratio by weight thereof being equal to or greater than 1.

15 Claims, No Drawings

RANEY-TYPE CATALYSTS FOR THE HYDROGENATION OF HALONITROAROMATIC COMPOUNDS

BACKGROUND OF THE INVENTION

1. Field of the Invention

The present invention relates to the catalytic reduction of halonitroaromatic compounds into haloaminoaromatic compounds via hydrogenation in the presence of catalysts based on modified Raney nickel.

The present invention especially relates to such modified Raney-type catalysts, per se.

2. Description of the Prior Art

Catalysts of Raney nickel are widely used in hydrogenation reactions. They are prepared by alkaline attack, using a concentrated base, on aluminum-rich aluminum/nickel alloys. This attack has the essential consequence of removing aluminum. The catalysts obtained are nickel crystallite agglomerates having a high specific surface and a variable residual aluminum content. In this respect, see the following literature references:

(a) M. Khaidar, C. Allibert, J. Driole and P. Germi, *Mat. Res. Bull.*, 17, 329–337 (1982);

(b) V. Birkenstock, R. Holm, B. Reinfandt and S. Storp, *J. Catal.*, 93, 55–67 (1985);

(c) J. Gros, S. Hamar-Thibault and J. C. Joud, *Surface and Interface Analysis*, 11, 611–616 (1988).

The reduction of halonitroaromatic compounds, such as 3-chloro-4-fluoronitrobenzene, into haloaminoaromatic compounds, such as 3-chloro-4-fluoroaniline, is of great importance in organic chemistry because it provides a key route in the production of pharmaceutically active principles.

One of the disadvantages in this reduction via hydrogenation in the presence of Raney nickel or similar compounds is a hydrodehalogenation side reaction downstream of the reduction of the nitro functional group. This reaction is carried out only by means of the halogenated aniline. Such hydrodehalogenation of the aniline nucleus results, in addition to its negative influence on the selectivity and the yield of the catalytic hydrogenation reaction, in the formation of particularly aggressive byproducts, especially vis-a-vis catalysts of Raney nickel type. These byproducts include, for example, hydrochloric acid, which has the effect of significantly decreasing the useful life of the catalyst. Hydrodehalogenation is particularly critical in the event of low substrate concentrations.

International Patent Application PCT 89/07,096 describes exactly this problem of catalytic hydrogenation of halonitroaromatic compounds. The process described therein features the use of a Raney catalyst based on cobalt/aluminum/nickel/chromium. Even though this process provides improvements with respect to catalysts of activated nickel or activated carbon/platinum type, optionally in combination with catalyst inhibitors, or also with respect to other catalysts of sulfur-modified platinum type, the hydrodehalogenation side reaction persists and continues to produce not insignificant amounts of undesirable halogenated byproducts and dehalogenated compounds.

Canadian Patent CA-961,834 describes Ni(85% to 96%)/Mo(0.5% to 10%)/Al ($\leq$14%) catalysts which can be used for catalytic hydrogenation, especially of carbonyl compounds such as, for example, acetone, nitrophenoxide, itaconate, and the like.

The substrates involved are different from those associated with the catalysts and the hydrogenation process in accordance with this invention. These catalysts are neither selective nor significantly active with respect to nitro radicals borne by aromatic nuclei. In addition, this patent is conspicuously silent as regards hydrodehalogenation.

Similarly, the article by S. Hamar-Thibault et al, *J. Chim. Phys.*, 88, 219–232 (1991), describes Raney catalysts doped with molybdenum and employed in the hydrogenation of acetophenone in the liquid phase. Here again, the problem of hydrodehalogenation is not encountered. In addition, this article also describes that the more the molybdenum content of the catalyst increases, the more the intrinsic activity and the specificity with respect to sites to be hydrogenated, i.e., carbonyls, decrease.

Among other catalytic hydrogenation starting materials which are not affected by the hydrodehalogenation side reaction, exemplary are the dinitroaromatic compounds reduced to diaminoaromatic compounds via the process described in DE-3,537,247. This particular hydrogenation process employs catalysts based on Raney nickel doped with molybdenum. These finished catalysts are depleted in aluminum, relative to the amount of Mo present, as is illustrated by the Al/Mo ratio, which is less than 1 (Al and Mo being expressed as % by weight) for the Raney catalysts described.

Finally, Raney catalysts are also known which are doped with a transition metal element. These Ni/Al/metal monodoped hydrogenation catalysts are used for the selective reduction of para-chloronitrobenzene to para-chloroaniline. The presence of a metal dopant in the Raney catalyst promotes a decrease in selectivity and a decrease in catalytic activity. Moreover, the dopant appears to increase hydrodehalogenation. The latter even remains significant for high paranitrochlorobenzene concentrations (case of iron and chromium). Thus, in a haloaromatic environment, doping Raney catalysts with a metal does not appear desirable.

SUMMARY OF THE INVENTION

Accordingly, a major object of the present invention is the provision of a Raney-type catalyst composition well suited for the catalytic hydrogenation of halonitoaromatic compounds into haloaminoaromatic compounds, which is very active and selective and which does not effect hydrodehalogenation side reactions, or, at the very least, limits such side reactions to the greatest possible extent.

Another object of the present invention is the provision of a Raney-type catalyst composition which exhibits excellent chemical behavior, both during storage and during reaction. Indeed, the subject catalysts are preferably insensitive to the reactants and to the products of catalytic hydrogenation.

Yet another object of this invention is the provision of a Raney-type catalyst composition which can be produced easily and economically.

Thus, it has now unexpectedly and surprisingly been determined that the use of molybdenum as a dopant in a conventional Raney catalyst, such molybdenum values advantageously being present in the catalyst in an exact and given amount with respect to the nickel and to the aluminum, provides those advantages indicated above.

Briefly, the present invention features a Raney-type catalyst composition for the catalytic hydrogenation of halonitroaromatic compounds into haloaminoaromatic compounds, comprising an alloy consisting essentially of Ni/Al/Mo, the Al/Mo ratio by weight of which is greater than or equal to 1, preferably greater than or equal to 2, and even more preferably ranging from 2.5 to 3.5.

DETAILED DESCRIPTION OF BEST MODE AND PREFERRED EMBODIMENTS OF THE INVENTION

More particularly accordingly to the present invention, the subject molybdenum-doped Raney-type catalysts are very active and selective. Moreover, they effect only very weak hydrodehalogenation. This side reaction phenomenon is quantitatively in fact at most half of that of the known prior art.

In addition, it is observed that the subject catalysts are not, in actual practice, attacked during the catalytic hydrogenaton reaction. Therefore, they exhibit very good chemical stability over time.

It is highly preferred that the Mo/(Ni+Al) ratio by mass [expression equivalent to the expression "ratio by weight" regarded as incorrect by academicians (in fact, it defines a ratio of amounts of matter and the ratio of weights is a ratio of forces)] is at least equal to 5%. It is also desirable that the Mo/Ni ratio by mass is at least equal to 3/40, preferably to 0.1.

The Ni/(Ni+Al+Mo) ratio is advantageously at least equal to 0.5.

One important characteristic is that the compositions according to the invention are advantageously produced by alkaline attack on a mother alloy containing more aluminum than the subject compositions.

Considering only the three principal elements nickel, molybdenum and aluminum, the catalytic compositions according to the invention contain Ni/Al/Mo in the following proportions by weight, expressed as % by weight:

(a) $50 \leq Ni \leq 78$, preferably $60 \leq Ni \leq 70$, (b) $20 \leq Al \leq 40$, preferably $25 \leq Al \leq 35$, and (c) $2 \leq Mo \leq 20$, preferably $5 \leq Mo \leq 15$.

The impurities are those typical in the material (in nature and in proportion). A more particularly preferred catalytic composition for the molybdenum-doped Raney-type catalyst is that which corresponds to a Ni/Al/Mo precursor alloy composition of 44%, 38% and 18% by weight, respectively.

After alkaline attack, it would appear that approximately half the aluminum remains whereas approximately two-thirds of the molybdenum is leached by the sodium hydroxide solution.

The compositions according to the present invention advantageously have, by mass, after mathematical rounding, about three times as much aluminum as molybdenum and seven times as much nickel as molybdenum (ratio 7/3/1), in particular the composition in the mass proportions Ni/Al/Mo=63/28/9 employed in Example 1.

The relative proportions of the constituents of the compositions according to the invention, and of the alloy from which same are prepared, are reported with the impurities excepted. Stated differently, this comprehends that it is advisable to take into account a certain tolerance to impurities (especially metal impurities) in the compositions and in the alloy.

The catalytic compositions according to the invention (also referred to simply as "catalysts") can be used pure or in combination with other materials, such as inert supports, under the conditions of use. Such a catalyst can be provided in various forms. It can be, for example, a monolithic substrate (honeycomb or otherwise) of composition Ni/Al/Mo, or a monolithic substrate coated with a layer of composition Ni/Al/Mo, or also can be in the form of divided products of, or coated with, the composition Ni/Al/Mo.

By "divided form" is intended pulverulent products (powders) and also articles produced by shaping these products (solid or hollow beads, pellets, spheres, granules, extrudates, agglomerates and others of circular, oval, trilobate or multilobate cross-section).

Catalysts of bead or pellet type and others present the advantage of being subsequently separated from the reaction medium very quickly, by simple settling. Catalysts of pulverulent type generally require a filtration stage for their separation.

Naturally, all of the aforementioned catalysts are selected with a specific surface suitable for the application under consideration. In actual practice, it is possible to use a Ni/Al/Mo composition whose specific surface, measured according to the BET (Brunauer, Emmett and Teller) method, can vary from one tenth to several hundreds, indeed several thousands, of square meters per gram and, in general, from 1 to 500 m$^2$/g. It most typically and preferably ranges from 10 to 100 m$^2$/g.

Thus, either commercially available tungsten carbides or tungsten carbides can be used which will have been synthesized according to any process per se known to this art.

The advantageous selectivity of the catalyst according to the invention is especially evident during hydrogenation reactions. Thus, according to the present invention, a selective hydrogenation reactant has now been found containing a catalytic composition and hydrogen whose partial pressure ranges from 1 to 100, preferably from 5 to 50, even more preferably from 15 to 25 bar (1 bar=10$^5$ Pa).

This selectivity is particularly marked with respect to starting materials selected from among halonitro(or nitroso)aromatic derivatives. These compounds advantageously have at least one nitro (or nitroso) group directly bonded to an aromatic carbon ring member and at least one halogen also directly bonded to an aromatic carbon ring member. Preferably, at least one halogen and at least one nitro group are bonded to the same aromatic radical (aryl), which can be a radical containing one ring or containing a number of fused rings.

Advantageously, there are at most 3, preferably at most 2, nitro or nitroso groups per aromatic radical.

Advantageously, there are at most 4, preferably at most 3, halogen atoms per aromatic radical.

Thus, the catalytic activity of the compositions according to the present invention is particularly advantageous for halonitro (or nitroso) aromatic compounds possessing one or a plurality of aromatic radical(s), preferably only one, and even more preferably, having the following formula:

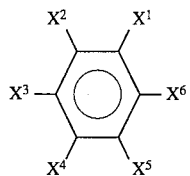

in which $X^1$ to $X^6$, which may be identical or different, are each H, a halogen, preferably F, Cl or Br, a radical NO$_x$, in which x=1 or 2, or, wherein R=H, aralkyl, aryl, alkenyl or linear or branched alkyl, or an alkali metal, preferably a methyl, ethyl, propyl, butyl, phenyl, benzyl or naphthyl radical, with the proviso that at least one of the radicals $X^1$ to $X^6$=halogen and at least one other=NO$_x$, in which x=1 or 2.

Exemplary halonitroaromatic compounds providing the best results include 3-chloro-4-fluoronitrobenzene, 3,4- and 3,5-dichloronitrobenzene, 2,4-difluoronitrobenzene and 4-fluoronitrobenzene.

It will also be appreciated that, among the possible substrates, mixtures containing one or a plurality of the above derivatives can be used. Indeed, reactions involving a number of substrates can be carried out to prepare mixtures difficult to separate, but which, once hydrogenated, are easier to separate.

The present invention also features a catalytic hydrogenation process in which the catalytic composition described above is employed. This process can be carried out in continuous or discontinuous fashion.

The amounts of catalyst employed in the subject process can vary according to many factors such as, for example, the specific activity of the catalyst under consideration, the reaction conditions, such as temperature, pressure or reaction time, the nature of the halonitroaromatic compounds to be hydrogenated and the methodology used.

Advantageously, when the reaction is carried out discontinuously, the catalyst is present in a proportion of at most 10% by weight with respect to the starting halonitroaromatic compound and preferably in a proportion of 2% to 5% by weight.

To ensure good selectivity of the catalyst operating discontinuously, it is advantageous to provide, in the reaction mixture, an amount of starting halonitroaromatic compound which remains greater than or equal to 5 ppm. In discontinuous operation, these quantitative thresholds can be used as reference for determining the reaction time.

Hydrogenation is carried out, in liquid phase, under temperature and pressure conditions readily determined by one skilled in this art.

For example, hydrogenation can be carried out:

(i) under a $H_2$ pressure, $P_{H_2}$, ranging from 1 to 100, preferably from 5 to 50, and even more preferably from 15 to 25 bar (1 bar=$10^5$ Pa), (ii) the reaction temperature ranging from 25° to 150°, preferably from 40° to 120°, more preferably from 55° to 80° C.

In respect of the reaction medium, it is preferable according to this invention, to employ an inert solvent for dissolving the starting halonitroaromatic compound.

It is also preferable, in the selection of the reaction solvent medium, to take account of the solubility of the final product haloaniline.

Indeed, given that hydrodehalogenation is limited via the process of the invention, the production of haloaniline is thus increased and it is advantageous that the totality of production remains combined in the solvent, such as to facilitate the recovery thereof.

Advantageously, the reaction solvent medium comprises at least one primary or secondary alcohol having up to approximately 4 carbon atoms and, more particularly, of methanol, ethanol or isopropanol. Polar aprotic organic solvents, such as dimethylacetamide and tetrahydrofuran, can be used in combination with the alcohol when the solubility characteristics of the reactants require same.

It will be appreciated that this reaction medium necessarily contains water, which is an inevitable product of the reaction under consideration. Moreover, it is possible to provide for the use of variable amounts of water as cosolvent. In actual practice, the reaction solvent medium is generally an alcohol containing 1 to 10, advantageously containing 1 to 4, carbon atoms, preferably methanol or ethanol.

The apparatus for carrying out the process of the invention is conventional.

It is important that the catalyst and the process according to the invention provide excellent selectivities for the hydrogenation of halonitroaromatic compounds into haloaminoaromatic compounds, while minimizing undesirable hydrodehalogenation reactions. The latter are known to disturb the hydrogenation reaction. In discontinuous operation, this disturbance occurs at the end of the reaction, i.e., at a time when the concentrations of starting materials become low. In continuous operation, the deleterious effects of hydrodehalogenation (which produce a hydrohalic acid capable of attacking certain elements of the catalyst) become apparent when the concentrations of nitro derivatives are less than or equal to 500 ppm and often less than or equal to 200 ppm.

One of the particularly advantageous applications of this invention is the preparation of haloaminoaromatic compounds especially useful in the pharmaceutical and agrochemical fields.

In order to further illustrate the present invention and the advantages thereof, the following specific examples are given, it being understood that same are intended only as illustrative and in nowise limitative.

EXAMPLE 1

Preparation of the catalysts

The reference Raney Nickel was prepared by alkaline attack on a commercial Ni/Al alloy (50/50% by weight). This precursor alloy comprised a mixture of $NiAl_3$, $Ni_2Al_3$ or NiAl phases and of the eutectic, which had different reactivities with respect to sodium hydroxide.

The catalysts used in these examples were prepared from relatively nickel-rich crystalline precursor alloys close to the $Ni_2Al_3$ base, doped with the addition element molybdenum: $Ni_{2-x}/Al_3/Mo_x$, wherein x=0.4±0.05.

The alkaline attack protocol was the following: 60 g of precursor were introduced in small amounts over a period of time of approximately 40 min into a three-necked, round-bottomed flask equipped with a reflux condenser and containing 400 ml of a boiling 6N sodium hydroxide solution. The solution was maintained at reflux for two hours. The solid was then washed with a boiling 1N sodium hydroxide solution and again heated to boiling for 2 h in a 6N NaOH solution. The catalyst was then washed in a series of NaOH solutions of decreasing concentrations (3N, 2N and 1N). It was stored in a 1N sodium hydroxide solution.

EXAMPLE 2

Catalytic hydrogenation of 3-C-4-FNB (A) Apparatus:

The apparatus used for the hydrogenation of 3-C-4-FNB in liquid phase included:

(i) a Sotelem-type stainless steel reactor, having a capacity of 250 ml, and equipped with a circulating water heating system and a stirrer system (propeller turbine driven by a magnetic system); it was equipped with a septum for introducing the reactants, with a manometer for establishing the gas pressure in the reactor and with a system of valves for introducing hydrogen, for purges ($V_2$) and for withdrawing samples ($V_3$), (ii) a pressure regulator, and (iii) a reserve of hydrogen equipped with a manometer and with a valve for isolating the system.

(B) Operating procedure:

(i) The catalyst 4 g of catalyst were weighed under methanol and then introduced into the reactor with 130 ml of methanol. The entire mixture was purged with a 150 ml×min$^{-1}$ hydrogen stream ($P_{H_2}$=1 bar) for 10 min.

(ii) The hydrogenation reaction

The temperature of the reaction medium was increased to 60° C. and the total pressure to 18 bars with H$_2$.

The stirring rate was maintained a 650 rev×min$^{-1}$.

These parameters remained constant throughout the duration of the test (5 h).

The reactant (3-C-4-FNB), dissolved as a 50/50 mixture in methanol, was injected into the reactor through the septum, using a pump, at a flow rate of 40 g/h.

The instant at which stirring was commenced was time zero of the reaction. The most typical experimental conditions were:

(1) weight of catalyst: 4 g, (2) total volume=150 ml, (3) 3-C-4-FNB/solvent=40 g/h, (4) $P_{H_2}$=17.5 bar, (5) stirring rate=650 rev×min$^{-1}$.

(C) Analysis of the reaction medium

The progress of the reaction was monitored by analyzing, via gas phase chromatography, samples of the reaction mixture withdrawn at regular intervals during the reaction:

(I) Perkin-Elmer 8410 flame ionization chromatograph, (II) temperature of the injector: 220° C., (III) temperature of the detector: 230° C., (IV) column used: 20% alcomine, Chromosorb GNAW 80/100, having a length of 4 m and a diameter of ⅛th of an inch, (V) column temperature: 80° C., (VI) flow rate of the carrier gas (N$_2$): 20 ml×min$^{-1}$, (VII) volume injected: 1 μl.

The content of unconverted nitro derivatives was monitored by polarography. The sensitivity of this method of measurement was greater than or equal to 5 ppm.

(D) Compounds employed

The catalyst was Mo-doped Raney Ni prepared according to the methodology described in Example 1 and having the following composition: Ni/Al/Mo=63/28/9 by weight.

The starting substrate was 3-chloro-4-fluoronitrobenzene assaying at 98.5%.

The reaction solvent medium was RP-grade Prolabo methanol.

(E) Results obtained:

The Table below reports the results obtained. Hydrodechlorination is reflected by the amount of chlorides produced, reduced to a molar percentage with respect to the nitro derivatives charged to the hydrogenation. No other organic compounds were formed than the desired haloaniline, the other analogous haloanilines and aniline.

TABLE

| TIME (h) | Weight of nitro compound hydrogenated (g) | Content of nitro compound (ppm) | % Amine hydrogenation output | % HDC Hydrodechlorination |
|---|---|---|---|---|
| 0 | 0 | 0 | 0 | 0 |
| 1 | 24 | 0 | 4.8 | 3.4 |
| 2 | 44 | 5 | 24.5 | 0.8 |
| 3 | 64 | 55 | 32.7 | 0.8 |
| 4 | 85 | 230 | 37.2 | 0.6 |
| 5 | 106 | 255 | 39.2 | 0.5 |

Moreover, analyses were carried out on the hydrogenation crude products and only approximately 9 ppm of nickel and less than 1 ppm of molybdenum and of aluminum were determined. It will therefore be concluded therefrom that the catalyst was not attacked during the reaction. This illustrates another significant advantage of the catalyst according to the invention.

EXAMPLE 3

The reaction was carried out as in Example 2, except that the 3-chloro-4-fluoronitrobenzene was replaced with 3,4-dichloronitrobenzene.

After continuously hydrogenating for 11 h at 75° C. at a total pressure of 15 bars, the hydrodechlorination yield was stable at 0.9% and the residual halonitrobenzene concentration was 100 ppm.

EXAMPLE 4

The reaction was carried out as in Example 3, except that the halonitrobenzene hydrogenated was 3,5-dichloronitrobenzene.

After the same hydrogenation time, under the same conditions and for the same content of residual nitro compound, the hydrodechlorination yield was 0.3%.

EXAMPLE 5

The reaction was carried out as in Example 2, except that the halonitrobenzene to be hydrogenated was 4-fluoronitrobenzene.

The hydrogenation was carried out a 100° C. under a total pressure of 20 bars.

The amount of catalyst and the nature and the amount of solvent used were unchanged.

The rate of injection of the 4-fluoronitrobenzene/methanol (50/50 w/w) mixture was adjusted to 100 g×h$^{-1}$.

The content of unconverted 4-fluoronitrobenzene was less than 100 ppm and no hydrodefluorination was detected.

EXAMPLE 6

The reaction was carried out as in Example 5, except that the 4-fluoronitrobenzene was replaced with 2,4-difluoronitrobenzene.

The results were identical to those of Example 5; no hydrodefluorination was detected.

EXAMPLE 7 (Comparative)

The reaction was carried out as in Example 2, but the catalyst of the invention was replaced with a conventional Raney nickel catalyst containing no other metal than residual aluminum (7.8% w/w); the hydrodechlorination yield was 6% after reaction for 5 h.

The level of residual nitro derivative was in the region of 200 ppm.

EXAMPLE 8 (Comparative)

The procedure of Example 7 was repeated, but the catalyst was a Raney nickel containing 0.8% iron, 2% chromium and 8.2% aluminum.

The hydrodechlorination yield attained a value of 7.5%, for a residual content of nitro compound in the region of 150 ppm.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A Raney catalyst composition consisting essentially of an alloy of nickel, aluminum and molybdenum, Ni/Al/Mo, the alloy having an Al/Mo ratio by weight thereof being equal to or greater than 1, and a Mo/(Ni+Al) ratio by mass thereof being at least 5%, and the nickel content being not greater than 78% by weight.

2. The Raney catalyst composition as defined by claim 1, said Al/Mo ratio being equal to or greater than 2.

3. The Raney catalyst composition as defined by claim 2, said Al/Mo ratio ranging from 2 to 3.

4. The Raney catalyst composition as defined by claim 1, the alloy having a Mo/Ni ratio by mass thereof being at least 3/40.

5. The Raney catalyst composition as defined by claim 4, said Mo/Ni ratio being about 0.1.

6. The Raney catalyst composition as defined by claim 1, the alloy having a Ni/(Ni+Al+Mo) ratio being at least 0.5.

7. The Raney catalyst composition as defined by claim 1, having the following proportions of Ni/Al/Mo, expressed as percentages by weight:

$50 \leq Ni \leq 78$, $20 \leq Al \leq 40$, $Mo \leq 20$, the Mo being present in an amount such that the Mo/(Ni+Al) ratio by mass thereof is at least 5%.

8. The Raney catalyst composition as defined by claim 7, having the following proportions of Ni/Al/Mo, expressed as percentages by weight:

$60 \leq Ni \leq 70$, $25 \leq Al \leq 35$, $5 \leq Mo \leq 15$.

9. The Raney catalyst composition as defined by claim 1, having the mass proportions Ni/Al/Mo of about 63/28/9, respectively.

10. The Raney catalyst composition as defined by claim 1, comprising a monolith.

11. The Raney catalyst composition as defined by claim 1, comprising a monolithic support substrate coated with a layer of said Ni/Al/Mo.

12. The Raney catalyst composition as defined by claim 1, comprising particulates thereof.

13. A shaped article comprising the Raney catalyst composition as defined by claim 1.

14. The Raney catalyst composition as defined by claim 1, wherein the Mo/(Ni+Al) ratio by mass is at least 6% and the composition includes $\leq 20$ weight % Mo.

15. The Raney catalyst composition as defined by claim 1, wherein the Mo/(Ni+Al) ratio by mass is at least 7% and the composition includes $\leq 20$ weight % Mo.

* * * * *